(12) United States Patent
Persing et al.

(10) Patent No.: US 6,258,320 B1
(45) Date of Patent: Jul. 10, 2001

(54) METHOD FOR PRESERVATION OF NUCLEIC ACIDS

(75) Inventors: David H. Persing, 2225 48th St. SW., Rochester, MN (US) 55902; Susan H. Persing, Rochester, MN (US)

(73) Assignee: David H. Persing, Sammamish, WA (US)

( * ) Notice: Subject to any disclaimer, the term of this patent is extended or adjusted under 35 U.S.C. 154(b) by 0 days.

(21) Appl. No.: 09/058,089

(22) Filed: Apr. 9, 1998

(51) Int. Cl.$^7$ ....................................... B01L 11/00
(52) U.S. Cl. ................... 422/40; 422/102; 435/2; 435/260; 435/307.1
(58) Field of Search ................. 422/40–43, 99, 422/102, 939, 940; 435/2, 6, 307.1, 260; 206/363

(56) References Cited

U.S. PATENT DOCUMENTS

| | | | |
|---|---|---|---|
| 5,593,883 | 1/1997 | Cano et al. | 435/252.1 |
| 5,853,662 | * 12/1998 | Watanabe | 422/40 |
| 5,856,102 | * 1/1999 | Bierke-Nelson et al. | 435/6 |
| 5,856,172 | * 1/1999 | Greenwood et al. | 435/260 |
| 5,885,524 | * 3/1999 | Watanabe et al. | 422/40 |

OTHER PUBLICATIONS

Bada, J.L., et al., "Amino Acid Racemization in Amber–Entombed Insects: Implications for DNA Preservation," *Geochimica et Cosmochimica Acta, 58*, 3131–3135 (1994).

Cano, R.J., "Analysing Ancient DNA", *Endeavour, 20*, 162–167 (1996).

Cano, R.J., et al., "Amplification and Sequencing of DNA from a 120—135–Million–Year–Old Weevil", *Nature, 363*, 536–538 (Jun. 10, 1993).

Cano, R.J., et al., "Isolation and Partial Characterisation of DNA from the Bee *Proplebeia dominicana* (Apidae: Hymenoptera) in 25–40 Million Year Old Amber", *Med. Sci. Res., 20*, 249–251 (Apr. 1992).

DeSalle, R., et al., "DNA Sequences from a Fossil Termite in Oligo–Miocene Amber and Their Phylogenetic Implications", *Science, 257*, 1933–1936 (Sep. 25, 1992).

DeSalle, R., et al., "Very Old DNA", *Current Opinion in Genetics and Development, 4*, 810–815 (1994).

Dimond, E., et al, "The Genetic Basis of Cancer", *Cancer Nursing, 20*, 213–226 (1997).

(List continued on next page.)

Primary Examiner—Jill Warden
(74) Attorney, Agent, or Firm—Schwegman, Lundberg, Woessner & Kluth, P.A.

(57) ABSTRACT

A method for long-term maintenance of intact nucleic acid is provided. The method comprises introducing a nucleic acid containing receptacle into a cavity of a storage device. The nucleic acid containing receptacle comprises an amount of isolated vertebrate nucleic acid in a cavity of the receptacle, wherein either the receptacle or storage device is formed of a natural material. The nucleic acid is retained in the cavity by a fastener. A sealant is introduced into the aperture of the cavity of the device to form a nucleic acid storage device.

15 Claims, 1 Drawing Sheet

OTHER PUBLICATIONS

Golenberg, E.M., et al., "Chloroplast DNA Sequence from a Micocene Magnolia Species", *Nature, 334,* 656–658 (Apr. 12, 1990).

Handt, O., et al., "Ancient DNA: Methodological Challenges", *Experientia, 50,* 524–529 (1994).

Hoss, M., et al., "DNA Extraction from Pleistocene Bones by a Silica–Based Purification Method", *Nucleic Acids Research, 21,* 3913–3914 (1993).

Lindahl, T., "Recovery of Antediluvian DNA", *Scientific Correspondence, Nature, 365,* 700 (Oct. 21, 1993).

Poinar, Jr., G.O., "Recovery of Antediluvian DNA", Reply to Lindahl, T., in *Scientific Correspondence, Nature, 365,* 700 (Oct. 21, 1993).

Poinar, Jr., G.O., "The Range of Life in Amber: Significance and Implications in DNA Studies", *Experientia, 50,* 536–542 (1994).

Quesnel, S., et al., "Genetic Prediposition to Cancer and Familial Cancer Syndromes", *The Pediatric Clinics of North America, 44,* 791–808 (Aug. 1997).

Soltis, P.S., et al., "An rbcL Sequence from a Miocene Taxodium (Bald Cypress)", *Proc. Natl. Acad. Sci. USA, 89,* 449–451 (Jan. 1992).

Thomas, W.K., et al., "DNA Sequences from Old Tissue Remains", *Methods in Enzymology, 224,* 406–418 (1993).

Walsh, P.S., et al., "Chelex® 100 as a Medium for Simple Extraction of DNA for PCR–Based Typing from Forensic Material", *BioTechniques, 10,* 506–513 (1991).

* cited by examiner

METHOD FOR PRESERVATION OF NUCLEIC ACIDS

BACKGROUND OF THE INVENTION

Amber is a natural, amorphous, polymeric glass which is formed from the fossilized resin of plants. The plant resins from which amber originates comprise complex mixtures of terpenoid compounds, acids, alcohols, and essential oils. As the resin ages, it becomes harder and forms a semifossilized product known as copal. Amber and copal are distinguished by their physical characteristics, e.g., melting point, hardness, and solubility. In particular, amber has mechanical, dielectric, and thermal features common to synthetic polymeric glasses.

Natural inclusions in amber represent organic material such as pieces of leaves or small insects that were trapped in the plant resins before the liquid resin hardened. The chemical structure of the resin changes during fossilization, e.g., the linking of isoprene units such as diterpenoids causes inert dehydration of organic materials present in the amber.

Insects trapped in amber have been studied for many years because they can provide valuable clues to entomologists regarding the phylogeny of species. Recently, it has been discovered that "ancient" DNA can be recovered from samples of insects or plants trapped in amber, even though the estimated age of the species has been over many millions of years in some cases (Cano, *Endeayor*, 20, 162 (1996); DeSalle and Grimaldi, *Current Op. Genet*, & *Devel.*, 4, 810 (1994); Poinar, *Experieltia*, 50, 536 (1994)). However, the ancient DNA in fossilized amber is often present at very low concentrations and may be quite degraded. While an amplification reaction, e.g., the polymerase chain reaction (PCR), can increase the concentration of DNA recovered from amber to detectable levels (Cano et al., U.S. Pat. No. 5,593,883), contamination during the DNA recovery process or subsequent analysis, and the presence of amplification inhibitors in the sample, e.g., tannins, porphyrins, heme and the like, can render PCR-derived results unreliable or unobtainable.

The integrity of ancient DNA which is embedded in amber may be compromised by oxidation of the DNA bases, a reaction that affects the ability of PCR to correctly amplify DNA sequences (Paabo et al., *J. Biol. Chem.*, 265, 4718 (1990)). Oxidation reactions, however, are not directly involved in the breakage of the DNA backbone. DNA integrity may also be affected by depurination (hydrolysis of the deoxyribose/adenine or guanine bond), followed by a β-elimination reaction that results in chain breakage. This reaction is thought to be the main reaction important in the fragmentation of DNA in the geologic environment. Nevertheless, based on studies of the retardation of the racemization of amino acids in insect tissues embedded in amber, Bada et al. (*Geochim. Cosmo. Acta*, 58,3131 (1994)) suggested that the breakdown of DNA embedded in amber might be inhibited.

Preservation of isolated and/or purified biological samples, e.g., isolated protein or nucleic acid, is often accomplished by storing the sample at low temperature, e.g., at −20° C. or −70° C. Low temperature slows natural biological and chemical processes, which can lead to the degradation of cellular components such as carbohydrates, proteins and nucleic acids. Moreover, the lower the temperature, the slower the degradation process. For example, complex cellular samples, e.g., sperm and eggs, are frozen and stored in a container having liquid nitrogen, which maintains the sample at about −200° C. However, to preserve the sample, the level of liquid nitrogen in the container must be carefully monitored and the container must be periodically replenished with liquid nitrogen.

Thus, there is a need for an improved method to preserve isolated vertebrate nucleic acid.

SUMMARY OF THE INVENTION

A system for the long-term storage or preservation of isolated nucleic acid derived or obtained from a vertebrate source, e.g., a mammal such as a human, is provided. Such long-term storage may be desirable for several reasons. First, the nucleic acid, present in largely intact form, may be used for retrospective genetic analysis. Second, the genomic nucleic acid content of a vertebrate represents a highly individualized biological substance that is unique to that particular organism. Storage of nucleic acid, preferably genomic DNA, in largely intact form would thus represent an identification means for that vertebrate. Also, the storage of genomic nucleic acid in intact form is desirable to provide a unique, personalized composition, for example, to wear as jewelry.

Thus, the invention provides a method for long-term maintenance of a sample of intact, isolated nucleic acid. The method comprises introducing an amount of isolated vertebrate nucleic acid into at least one recess, cavity or hollow of a receptacle. The nucleic acid may be genomic DNA, RNA or cDNA derived from RNA. As used herein, the term "derived" with respect to a RNA molecule means that the RNA molecule has complementary sequence identity to a particular DNA molecule. Preferably, the nucleic acid is genomic DNA obtained from a mammalian physiological sample, e.g., genomic DNA isolated from mammalian peripheral blood cells. The isolated nucleic acid sample represents a population of molecules, preferably a population which has not been subjected to an in vitro enzymatic amplification reaction.

A preferred receptacle of the invention is hollow and has an aperture or opening to permit access to the hollow interior of the receptacle. After introducing the nucleic acid sample into the recess, cavity or hollow interior of the receptacle, a fastening means or sealant is then placed into the aperture or opening of the receptacle leading to the recess, cavity or interior of the receptacle to form a nucleic acid containing receptacle. Thus, the fastening means or sealant retains the nucleic acid in the recess, cavity or interior of the receptacle.

Prior to the introduction of the fastening means, the nucleic acid containing receptacle is optionally subjected to conditions which reduce, inhibit or prevent the degradation of the nucleic acid, e.g., dehydration and/or the replacement of an oxygen-containing atmosphere (air) with an inert gas, such as argon or nitrogen. Subsequent to the fastening or sealing step, the nucleic acid containing receptacle is placed into a recess, cavity or hollow of a storage device. A second fastening means or sealant is then introduced into the aperture of the recess, cavity or hollow so as to retain the nucleic acid containing receptacle in the recess, cavity or hollow, thus yielding a nucleic acid storage device.

Also provided is a method to prepare a support device for long-term storage of vertebrate nucleic acid. The method comprises introducing a nucleic acid containing receptacle into a recess, cavity or hollow of a storage device. The nucleic acid containing receptacle comprises a depot or receptacle, e.g., a hollow sphere, having an amount of isolated vertebrate nucleic acid in a recess, cavity or hollow of the depot or receptacle. The isolated nucleic acid is retained in the recess, cavity or hollow by a fastening means such as a screw or preformed plug. A sealant is introduced into the aperture of the hollow of the device so as to retain the nucleic acid containing receptacle in the recess, cavity or hollow of the device, yielding a nucleic acid storage device.

Further provided is a nucleic acid storage device prepared by the methods of the invention. The device may be the basis for a jewelry product, e.g., in a ring, bracelet, earring or necklace, a decorative item, e.g., a mantelpiece, or as a form of identification.

The invention also provides a method for long-term maintenance of intact nucleic acid. In this embodiment of the invention, an amount of isolated vertebrate nucleic acid is introduced into a recess of a receptacle through an aperture. The aperture of the recess is then sealed so that the nucleic acid is retained in the recess. This yields a nucleic acid containing receptacle. It is preferred that the receptacle is formed from amber or copal.

Yet another embodiment of the invention is a method in which an amount of isolated vertebrate nucleic acid and an amount of a molten resin, e.g., molten copal, are introduced into a mold. When the mixture has hardened, a nucleic acid containing receptacle is obtained.

The receptacles and devices of the invention are particularly useful in retrospective genetic analyses. To perform such analyses, prior to recovery of the nucleic acid, the surface of the device or receptacle is sterilized. Depending on the material employed to form the device or receptacle of the invention, and the method employed to recover the isolated nucleic acid, the device or receptacle may remain essentially intact. For example, if the nucleic acid sample is embedded in amber, recovery of a portion of the sample for analysis may be accomplished without destroying the entirety of the device or receptacle. This can be accomplished by drilling a small hole through the amber and using a small, flexible tube attached to a syringe to recover a portion of the nucleic acid sample. The recovered nucleic acid is then analyzed for the presence or absence of a particular gene(s) or nucleic acid sequence(s), as described below. The high state of dehydration during storage in amber, along with the concurrent increase in salt concentrations during recovery of the nucleic acid, inhibits nucleases and preserves the nucleic acid, thus permitting molecular genetic analysis of the recovered nucleic acid, as described below.

Thus, the invention provides a method to identify the presence of an infectious agent in a vertebrate nucleic acid sample obtained from a nucleic acid storage device or receptacle, wherein the sample is suspected of containing a nucleic acid molecule of an infectious agent. The method comprises contacting an amount of a nucleic acid sample recovered from a device or receptacle of the invention with an amount of at least one, preferably at least two, oligonucleotides under conditions effective to amplify a nucleic acid molecule of the infectious agent so as to yield amplified DNA, e.g., by a polymerase chain reaction. Preferably, at least one oligonucleotide is specific for the nucleic acid molecule of the infectious agent. Then the presence of the amplified DNA is detected or determined. The presence of the amplified DNA is indicative that the vertebrate from which the sample was obtained was infected with the agent. Such a method is useful in retrospective studies where, for example, an infectious agent was identified, or its association with a particular disease is recognized, only after the nucleic acid sample was placed in the device or receptacle.

Also provided is a method to detect amplification of a preselected gene in a nucleic acid sample suspected of containing an amplified gene or an amplified sequence. The method comprises contacting a first amount of a labeled probe comprising at least a portion of the preselected gene with a nucleic acid sample suspected of containing an amplified gene or sequence, for a sufficient time to form binary complexes between at least a portion of said amount of probe and the sample, wherein the sample is recovered from a device or a receptacle of the invention. The amount of binary complexes formed is compared to the amount of binary complexes formed between at least a portion of a second amount of said probe and a control sample which does not contain an amplified gene, or a control sample having a "normal" content of the particular sequence. A greater amount of binary complexes formed with the recovered sample is indicative of amplification of the gene or sequence. For example, some genetic abnormalities are associated with gene amplification, e.g., N-myc in some neuroblastomas or the number of CAG repeats in the CAG repeat region of the SCA1 gene in autosomal dominant spinocerebellar ataxia type 1. Thus, the method of the invention may be employed to detect the amplification of certain sequences, e.g., CAG repeats, from a nucleic acid sample present in a device or receptacle of the invention, wherein the sample is obtained from an individual suspected of having a particular disorder, e.g., spinocerebellar ataxia type 1, or a similar, related disorder.

Alternatively, or in addition, the amount of binary complexes formed is compared to the amount of binary complexes formed between at least a portion of an amount of a second labeled probe which does not comprise the gene, but which represents a sequence of a single copy gene, and a second amount of the sample. A greater amount of binary complexes formed with the first probe is indicative of amplification of the gene. Methods to detect an amplified gene are useful in retrospective analyses to correlate a particular disease with an amplified gene or in family studies to determine if a particular amplified region was inherited through the germ line.

The invention also provides a method to detect genetic rearrangements of a preselected gene in a nucleic acid sample suspected of containing a genetically rearranged gene. Thus, this embodiment of the invention comprises contacting an amount of a labeled probe comprising at least a portion of the preselected gene with nucleic acid recovered from a device or receptacle of the invention, for a sufficient time to form binary complexes between at least a portion of said probe and the recovered nucleic acid. Then the absence or presence of said binary complexes formed is compared to the absence or presence of control binary complexes formed between at least a portion of a second amount of said probe and nucleic acid obtained from cells that do not contain a genetically rearranged gene. Complexes formed with the recovered nucleic acid which are different than complexes formed with control nucleic acid are indicative of a genetically rearranged gene. For example, chronic myelogenous leukemia (CML) is characterized at the molecular level by a translocation between c-ABL on chromosome 9 and BCR (break point cluster region) on chromosome 22. The BCR/ABL translocation results in the production of a protein, $P210^{BCR/ABL}$, which causes the malignant transformation of hematopoietic cells. Therefore, the method of the invention may be employed to detect genetic rearrangements, such as those found in CML.

Also provided is a method to determine genetic alterations or rearrangements of a preselected gene in a nucleic acid sample suspected of containing a genetically altered or rearranged gene. The method comprises subjecting nucleic acid, e.g., DNA, recovered from a device or receptacle of the invention to an amplification reaction such as a polymerase chain reaction, using a plurality of primers under reaction conditions sufficient to amplify at least a portion of said gene to produce an amplification product. Then it is determined whether the amplification product is different than an amplification product obtained by subjecting DNA which is isolated from a control sample which does not comprise alterations or genetic rearrangements of the gene to a polymerase chain reaction using the plurality of said primers under the same reaction conditions. The amplification product may be analyzed, for example, by sequence analysis or restriction endonuclease analysis, e.g., to detect a point mutation in the gene, or by gel electrophoresis and/or Southern blot analysis, e.g., to detect rearrangements, insertions or deletions in the gene. Examples of disorders associated with genetic alterations or rearrangements include, but are not limited to, those described in Quensel et al., *Pedia. Clinics of North Am*, 44, 791 (1997), and Dimond et al., *Cancer Nursing*, 20, 213 (1997). Moreover, similar methods may be employed in family linkage analyses.

BRIEF DESCRIPTION OF THE FIGURES

FIG. 1 depicts exemplary nucleic acid storage devices of the invention. (A) A cubic shaped device of the invention (b) having an oblong receptacle (a) inserted therein. A cavity or hollow of the receptacle contains isolated nucleic acid that is retained therein via a fastening means (shown as a darkened oval). (B) A triangular shaped device of the invention (b) having an oblong receptacle (a), a cavity or hollow of which contains isolated nucleic acid that is retained therein via a fastening means. (C) A cubic shaped device of the invention (b) having a spherical receptacle (a).

DETAILED DESCRIPTION OF THE INVENTION

Definitions

Figure 1A:
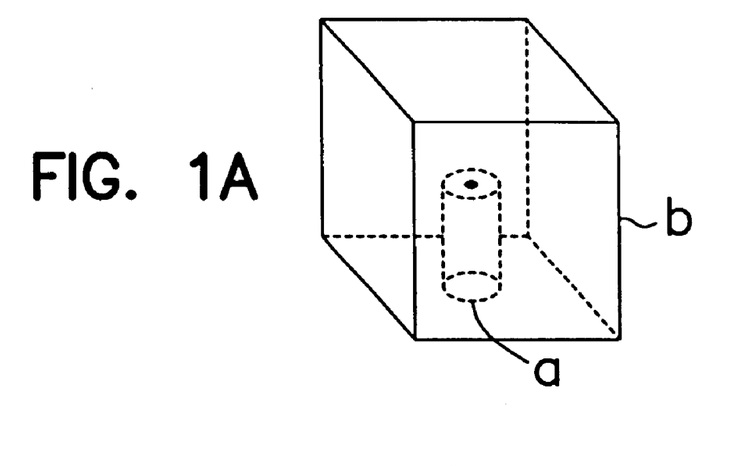
Figure 1B:
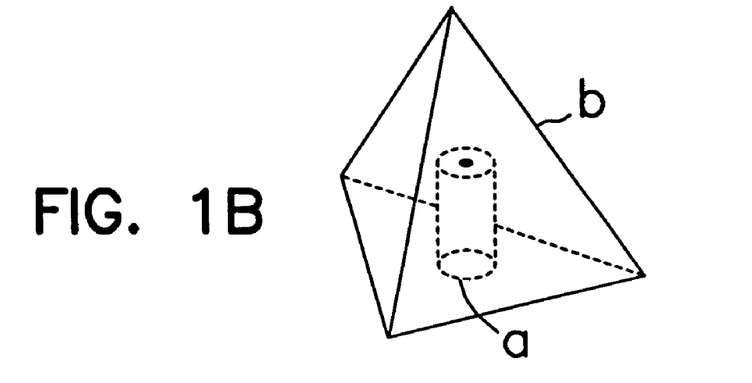
Figure 1C:
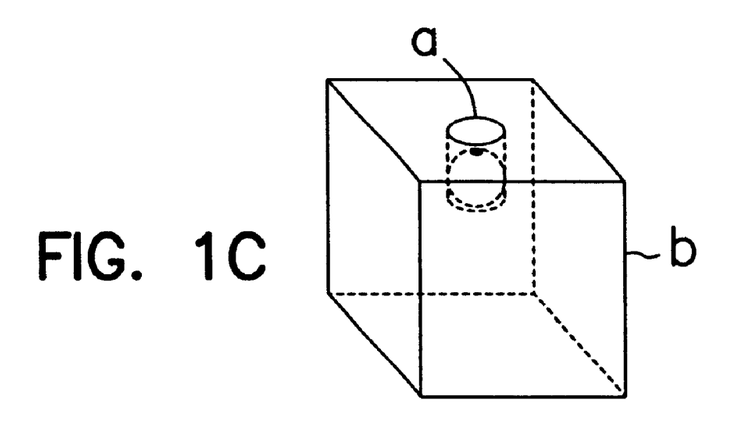

As used herein, a "storage device" or "device" within the scope of the invention is a device formed from a synthetic or natural material that prevents chemical or oxidative attack of nucleic acid and provides resistance to elemental breakdown, i.e., a material having nucleic acid protective properties. Preferably, the material is a resin. Preferred resins include, but are not limited to, amber and copal, as well as other resins having at least one hyperisometric agent, or mixtures thereof. Hyperisometric agents include sugars, e.g., glucose, galactose and arabinose alcohols (fenehyl, cis-communol, and trans-communoe); terpenes such as α-pinine, limonene and dipentene, and oxygenated derivatives of terpenes (aldehydes) and hydrogenated derivatives, e.g., methane derivatives, glycol ethers, and esters (agathic acid-monomethyl ester). The device of the invention may have a preformed shape, e.g., spherical, oval, cubic, or pyramidal, which preferably has a preformed recess, cavity, hole or hollow for receipt of the nucleic acid containing receptacle or depot, although the device is not limited to a preformed shape.

A "receptacle" or "depot" as used herein is formed from a synthetic or natural material. Preferably, the material is translucent. Alternatively, the material may be opaque. Also preferably, the material blocks the deleterious effects of UV radiation on nucleic acids such as DNA. The receptacle may comprise a preformed shape, e.g., spherical, oval, cubic, or pyramidal, having a recess, hole or hollow, although the receptacle is not limited to a particular preformed shape. Preferred materials from which to prepare the receptacle of the invention include precious and nonprecious metals, as well as synthetic materials such as synthetic polymers, e.g., plastic or resins. Preferred natural materials include amber, copal, pearl, mother of pearl, shell, ivory or precious or nonprecious stones.

If a receptacle of the invention is formed from a material having nucleic acid protective properties, the device within which that receptacle is placed may be formed from a material other than one with protective properties, e.g., a semi-precious stone or metal supporting structure. If a device of the invention is formed from a material having nucleic acid protective properties, the receptacle within the device may be formed from either a protective or non-protective material. Nonprotective materials may include the synthetic or natural materials described above.

A "sealant" as used herein, includes, but is not limited to, molten copal, balsam, e.g., Canadian balsam, epoxy, shellac or plastic.

As used herein with respect to a nucleic acid sample, the term "isolated" refers to in vitro isolation of intact nucleic acid from its natural cellular environment, and substantially free, e.g., at least greater than 90%, from association with other components of the cell, such as water, carbohydrate or protein, so that it could be sequenced, replicated, e.g., amplified, and/or expressed, and is free from nucleic acid degrading enzymes. For example, "isolated human genomic nucleic acid" is RNA or DNA generally containing greater than 200, preferably greater than 1000, and more preferably greater than 5000 or more, contiguous nucleotide bases.

As used herein, a nucleic acid sample which is "recovered" from a device or receptacle of the invention is RNA or DNA containing greater than about 200, preferably greater than about 1000, and more preferably 5000 or more, sequential nucleotide bases. The analysis of recovered DNA may include the excision or modification of the DNA by chemical means, e.g., by the use of restriction endonucleases, so that it can be analyzed, e.g., by restriction fragment length polymorphism (RFLP) or Southern blot analysis, or further manipulated, e.g., amplified. Amplified DNA may be isolated by electrophoretic separation on a polyacrylamide or agarose gel. The fragment of interest, e.g., an amplified gene, may be identified by comparison of its mobility versus that of marker DNA fragments of known molecular weight, removal of the gel section containing the desired fragment, and separation of the gel from DNA. See Lawn et al., *Nucleic Acids Res.*, 9, 6103 (1981), and Goeddel et al., *Nucleic Acids Res.*, 8, 4057 (1980). The purified DNA fragment may be sequenced using conventional methods, or cloned into a vector and then sequenced. Recovered RNA is preferably analyzed by reverse-transcriptase PCR (RT-PCR).

Sources and Isolation of Nucleic Acid

Sources of nucleic acid from which nucleic acid can be isolated for use in the invention include nucleic acid from any vertebrate, preferably mammalian, cellular source. Preferred mammalian sources include humans and wild, zoo or domestic animals, e.g., pets such as dogs, cats and birds, although the invention is not limited to any particular vertebrate or mammal. Preferred sources are those which yield large amounts of nucleic acid. These sources include, but are not limited to, blood cells or cell lines derived therefrom, tissues samples, e.g., biopsy material, or cell lines derived therefrom. Smaller samples may be collected by swab from any source, e.g., from body surfaces including skin and mucosa (nasal or oral swabs), or by swab-based absorption of body fluids such as blood.

Prior to nucleic acid isolation, the sample may be placed in a collection vessel having a preservative (EDTA) to eliminate nuclease, e.g., DNAse, activity. Additional preservative agents such as detergents may also be included in the sample collection vessel. To isolate a nucleic acid, preferably genomic DNA, standard methods, such as those described by Sambrook et al., *Molecular Cloning: A Laboratory Manual*, Cold Spring Harbor, N.Y. (1989), can be employed, although any method known to the art may be used. For example, to recover high molecular weight DNA from a sample, the sample is subjected to treatment with detergents such as SDS, proteases such as protease K, and chaotropic agents such as guanidinium isothiocyanate. Colored glycogen may be added so as to provide a visible carrier. A visible carrier is useful during recovery of the sample from the device or receptacle. The DNA is precipitated by the addition of an equal volume of isopropanol for 10 minutes at room temperature. Then the DNA is pelleted out of solution by high speed centrifugation, the aqueous alcohol solution is aspirated without disturbing the pellet, and the pellet is allowed to partially dry. A volume of triple-distilled water (e.g., 5–500 $\mu$l) is then added to resolubilize the DNA-glycogen mixture to form the isolated nucleic acid sample. The sample, or a portion thereof, is then introduced into a recess of a receptacle of the invention.

Another isolation method employs Chelexe® 100 (BioRad, Richmond, Calif.). Chelex® 100 is a chelating resin that has a high affinity for polyvalent metal ions. The Chelex resin is composed of styrene divinylbenzene copolymers containing paired iminodiacetate ions, which act as chelating groups. Chelex may prevent the degradation of DNA at high temperature by chelating metal ions that may act as catalysts in the breakdown of DNA at high temperatures in low ionic strength solutions. The alkalinity of Chelex suspensions (pH 10–11) and the exposure to 100° C. temperatures result in disruption of the cell membranes and denaturation of the DNA. Because these Chelex procedures result in denatured sample DNA, the DNA is not suitable for RFLP analysis after recovery.

For tissue sources, generally, a portion of tissue measuring about 1–2 mm in diameter is suspended in 500 $\mu$l of a 5% aqueous suspension and incubated for 2–4 hours at 56° C. with continuous shaking. Samples are then mixed for 30 seconds and placed in a dry bath at 95° C. for 5 minutes. After centrifugation at top speed in a microcentrifuge for 5 minutes, a portion of the supernatant containing extracted DNA is introduced into a receptacle or may be stored at −20° C. in a sterile microcentrifuge tube prior to introduction to the receptacle of the invention.

For whole blood (fresh, refrigerated or frozen), the following isolation procedure may be used:
1. Pipet 1 ml of sterile distilled water into a sterile 1.5 ml microcentrifuge tube. Add one of the following, and mix gently 3 $\mu$l whole blood.
2. Incubate at room temperature for 15–30 minutes. Mix occasionally by inversion or gentle vortexing.
3. Spin in a microcentrifuge for 2–3 minutes at 10,000–15,000×g.
4. Carefully remove supernatant (all but 20–30 $\mu$l) and discard.
5. Add 5% Chelex to a final volume of 200 $\mu$l.
6. Incubate at 56° C. for 15–30 minutes.
7. Vortex at high speed for 5–10 seconds.
8. Incubate in a boiling water bath for 8 minutes.
9. Vortex at high speed for 5–10 seconds.
10. Spin in a microcentrifuge for 2–3 minutes at 10,000–15,000×g.
11. Store the remainder of the sample at 2° C.–8° C. or frozen.

For DNA extraction from oral swabs:
1. Dissect swab into thirds using a scalpel equipped with a fresh, disposable blade. Use a clean cutting surface for each different sample.
2. Pipet 1 ml of sterile distilled water into a sterile 1.5 ml microcentrifuge tube. Add swab cutting to tube.
3. Incubate at room temperature for 30 minutes.
4. Twirl the swab with a sterile toothpick for at least 2 minutes to agitate the cells off the substrate. Remove the swab and toothpick.
5. Spin in a microcentrifuge for 2 minutes at 10,000–15,000×g.
6. Without disturbing the pellet, remove and discard all but 50 $\mu$l of the supernatant using a microtip disposable transfer pipet. Resuspend the pellet in the remaining 50 $\mu$l by stirring with a sterile pipet tip.

For DNA extraction from a hair sample:
1. Handle hair with clean forceps, examine the hair under a dissecting microscope for the presence of sheath material. The hair may be placed on a clean piece of white or black paper.
2. Wash the hair to reduce surface dirt and contaminants by immersing the hair in sterile, deionized water in a sterile plastic disposable beaker.
3. Return the hair to the dissecting microscope. Use a clean scalpel to cut a 1 cm portion from the root end of the hair. Because hair may contain cellular material on the surface which may or may not originate from the hair donor, it is advisable to cut off a 1 cm section of the shaft adjacent to the root portion for separate analysis as a control.
4. Add the root portion of the hair to 200 $\mu$l of 5% Chelex in a 1.5 ml microcentriftige tube.
5. Incubate at 56° C. (at least 6–8 hours) or overnight.
6. Vortex at high speed for 5–10 seconds.
7. Incubate in a boiling water bath for 8 minutes.
8. Vortex at high speed for 5–10 seconds.
9. Spin in a microcentrifuge for 2–3 minutes at 10,000–15,000×g.
10. Store the remainder of the sample at either 2° C.–8° C. or frozen.

To extract DNA from cultured or buffy coat cells:
1. Add up to 0.5 ml of cells to a 1.5 ml microcentrifuge tube; add 1 ml PBS buffer and centrifuge for 1 minute at 10,000–15,000×g (maximum speed) at room temperature. Remove supernatant and discard supernatant.
2. Resuspend the cells in 50–100 $\mu$l of sterile distilled water.
3. Add a volume of cell suspension to 200 $\mu$l of 5% Chelex such that the final cell concentration is about 25 cells/$\mu$l (5000 cells total). Mix gently.
4. Incubate at 56° C. for 15–30 minutes. Vortex at high speed for 5–10 seconds.

For RNA isolation, RNA may be isolated by any method known to the art. See, Sambrook et al., supra. cDNA may be prepared from isolated RNA using reverse transcriptase in a reverse transcriptase reaction.

Prior to introduction into the receptacles of the invention, a portion of the nucleic acid may be analyzed for integrity (e.g., by agarose gel electrophoresis), or subjected to assays to identify the presence of particular "markers", such as HLA typing (Begovich et al., *JAMA*, 273, 586 (1995); Erlich et al., *Arch. Path. & Lab. Med.*, 117, 482 (1993)). It is also preferred that the nucleic acid is quantitated by standard methods, e.g., $A_{260}/A_{280}$ ratio.

Preparation of a Device or Receptacle of the Invention

A preferred device of the invention is formed from amber or copal, or a similar naturally occurring resin. Amber can be purchased from several sources worldwide. Baltic amber, derived from deposits approximately 130 million years old, is harder than South American amber, which dates to a more recent period. This age is reflected in the hardness of the amber and its general workability. Other types of amber useful to prepare the present devices and for use in the methods described herein include, but is not limited to, Mexican, Dominican, Chinese, Canadian, Siberian and Lebanese amber. However, if the receptacle is formed from a material that has protective properties, the device can be formed from any desired material.

A spherical, oval, cubic, pyramidal or other shape is obtained or generated from raw material, e.g., amber, by the use of common shop equipment such as a band saw and abrasive wheel or stone. The minimum size of the device or receptacle is dictated by maximum achievable distance from the outside edge to a point within the center of the device. In general, the minimum distance from the center or midline of the device or receptacle should be at least about 3 millimeters, since this is the approximate thickness to achieve the protective properties of amber, although other thicknesses are envisioned. The machined device is free of fissures or organic material that, if decomposed by oxidation, could lead to a breach of continuity of the 3 mm amber wall from midline to outside.

A hole or recess is drilled into the shaped amber, preferably from the bottom to maintain visual appeal, but any side is acceptable as long as structural integrity is maintained and the recommended thickness of amber is achieved for adequate protection of the nucleic acid sample. Preferably, the hole is cylindrical. The depth of the cylinder or recess is such that at least about a 3 mm thickness of amber is maintained on all sides of the outside edges of the cylinder.

The receptacle of the invention, when it is placed into a cavity, hole or hollow of a storage device, protects the isolated nucleic acid from the potentially damaging effects of the material, e.g., molten copal, used to seal the aperture of hole or hollow. If a colored carrier is not employed in the preparation of the isolated nucleic acid, a receptacle can provide an easily visualized location of the nucleic acid, as the amount of isolated nucleic acid introduced into the recess may be nearly invisible to the eye. The receptacle may further protect the nucleic acid from potentially damaging UV light, and from mechanical loss when the isolated nucleic acid is subsequently recovered from the receptacle for analysis.

The receptacle may be formed or constructed of a synthetic material, such as plastic or imitation pearl, or it may be derived from a naturally occurring material, such as a cultured or natural pearl, a semiprecious stone or a piece of amber. Generally, the receptacle is modified to provide a recess into which the isolated nucleic acid is placed. The isolated nucleic acid is introduced into the hole or recess, e.g., using a small gauge needle or micropipette tip, and the hole or recess sealed with a natural or synthetic resin, preferably with molten copal, or a plugging or fastening means. For example, an amber piece may be bored out to receive the sample, e.g., a 10 microliter sample, and modified in a manner so as to accept a means for sealing off the recess, e.g., tapped so as to accept a small 1 or 2 millimeter jewelry screw or miniature bolt.

The receptacle is then placed into a 50° C. vacuum oven for 30 minutes. After removal from the oven, the receptacle is optionally placed into a container such as a plastic glove tent which contains an inert gas. The inert gas replaces the oxygen atmosphere, e.g., the oxygen is replaced with a 100% argon or nitrogen atmosphere. After 10 minutes of atmospheric equilibration, the receptacle is sealed with a plugging means, e.g., a chrome-plated screw or plastic plug, and removed from the container. In this manner, the inert gas is trapped in the recess by the plugging means. The inert atmosphere further protects against oxidative loss of nucleic acid over time. Once the receptacle is placed inside a storage device, such as a device formed from amber, degradation of the nucleic acid is negligible.

The nucleic acid containing receptacle is preferably introduced into a hole or hollow of a storage device formed from a material having nucleic acid protective properties, e.g., amber or copal. It is envisioned that more than one nucleic acid containing receptacle may be placed into a hole or hollow of a storage device. Likewise, a device may be formed so as to have more than one hole or hollow, each of which may have more than one receptacle of the invention. In this manner, multiple samples of the nucleic acid are stored, maintained and preserved such that removal of one receptacle does not affect the integrity of the nucleic acid in other receptacles.

A further embodiment of the invention is the preparation of a receptacle in which molten copal and isolated nucleic acid are mixed together in a mold, e.g., to form a bead.

To determine whether a particular device or receptacle is useful to store or preserve nucleic acid, a device or receptacle having a test sample is subjected to conditions which degrade nucleic acids, e.g., nucleases, solutions of chlorine bleach, and ultraviolet light. The nucleic acid is then recovered (see below) and analyzed for integrity. Devices or receptacles that fall within the scope of the invention include those formed from materials that inhibit the degradation of a nucleic acid sample by about at least 50% to at least about 80%.

Recovery of Nucleic Acid from a Receptacle or Device Formed from Amber or Copal

The method employed to recover nucleic acid from a device or receptacle of the invention will depend on the material(s) from which the receptacle or device is formed and whether it is desirable to retain a portion of the device or receptacle in an intact form. Thus, for a receptacle formed from a mixture of molten copal and isolated nucleic acid, the receptacle is pulverized in order to extract the nucleic acid. For receptacles having certain fastening means, the fastening means is easily removed, e.g., a screw. Alternatively, the nucleic acid within an amber device or receptacle may be recovered by drilling through the amber and recovering the nucleic acid with a needle, e.g., a tuberculin needle after rehydration of the sample with nuclease-free water.

Various methods for isolating nucleic acid from a receptacle or device may be employed provided that adequate containment and contamination safeguards are employed. One such safeguard involves sterilization of the outer surface of a device or receptacle of the invention.

In a preferred embodiment of the invention, the outer surface of a device or receptacle formed from amber is sterilized as follows: the amber device or receptacle is: (1) immersed in 2% phosphate buffered glutaraldehyde at 35° C. for 12 hours in vacuo; (2) rinsed three to four times in sterile, double distilled water (SDDW) or phosphate-buffered saline and then culturing the rinse water on Trypticase Soy agar (TSA) (BBI, Cockeysville, Md.) to evaluate the effectiveness of the sterilization procedure; (3) immersed in 10% bleach for an additional 6 hours at 37° C.; (4) rinsed three times in SDDW and then culturing the rinse water on TSA to evaluate the effectiveness of the sterilization procedure; (5) immersed in 70% ethanol for 2 hours at 35° C.; and (6) exposed to flames to evaporate the alcohol. Alternatively, after step (1), the amber device or receptacle is immersed in 70% ethanol for 30 minutes, flamed to burn off the ethanol and then rinsed twice with sterile PBS. A sample of the surface-sterilized amber is cultured onto Trypticase Soy Broth (TSB) to evaluate the sterilization process.

Other methods of sterilizing and/or decontaminating amber and/or other naturally occurring resin samples include plasma etching, sonication, fixatives, solvents, gas fumigation, application of a sporicidal agent and removing the outer layer of the resin from the sample.

Nucleic acid is then extracted using sterile instruments, sterile techniques, and sterile conditions. For example, amber may be cracked after freezing in liquid nitrogen and the addition of a few drops of hot, sterile, physiological saline in order to expose the nucleic acid sample. Sterile dissecting needles are used to pry open the cracked amber, if necessary. Additionally, samples with or without a visible sample may be ground and/or pulverized into powder or semi-powder material under sterile conditions following decontamination of the sample's surface. The samples may be ground into a powder or semi-powder by any number of methods, including use of sterile sand or a mortar and pestle.

Less destructive and more targeted methods of isolation may provide the dual advantages of sample preservation and control over which part of the sample is recovered. Such methods may include, for example, the use of hollow-bore micro-drills capable of extracting very small samples without destroying the entire sample. Such methods may further include use of techniques for freezing the resin sample, directed laser(s), use of sterile sand to grind the sample into powder, heat, use of a sterile pulverizing press and chemical treatment. Hydration of the resin may facilitate sample extraction.

The nucleic acid may be removed with the aid of tuberculin syringes outfitted with sterile, 27-gauge needles. The dried sample may be resuspended in 100 $\mu$l of TE buffer (10 mM TrisHCl (pH 8.0), 1 mM EDTA) and stored at −70° C. until processed. DNA may be further purified according to the methods described in Sambrook et al., supra.

A DNA extraction protocol that is useful for samples embedded in a resin is a modification of the protocol initially published by Blin and Stafford (N. Blin et al., *Nucleic Acids Res.*, 3, 2303 (1976)). Approximately 0.1 g of small pieces containing the nucleic acid from the resin is added to 0.5 to 5 ml of extraction buffer containing 10 mM Tris-HCl (pH 8.0), 2 mM ethylenediaminetetraacetic acid (EDTA), 10 mM NaCl, 1% (w/v) sodium dodecyl sulfate (SDS), 10 mg/ml dithiothreitol (DTT), and 0.5 mg/ml proteinase K. Incubation at 37° C. with gentle agitation overnight allows most or all of the sample to go into solution. An equal volume of phenol, equilibrated with 1 M Tris-HCl (pH 8.0), is added. Two phenol extractions and one chloroform extraction are performed, and the water phase is concentrated and purified on a Centricon 30 microconcentrator (Amicon, Danvers, Mass.). The retentate can be stored frozen, preferably in a few aliquots. In all cases, solutions should be manipulated with nuclease-free, e.g., DNAase-free, positive displacement pipettes.

Recovered nucleic acid is quantitated spectrophotometrically. Only samples with $A_{260}/A_{280}$ ratios $\geq 1.8$ are used. If sufficient quantities of nucleic acid are recovered, agarose gel electrophoresis of the samples and staining of the gel for 1 hour in a 0.5 $\mu$g mL$^{-1}$ solution of ethidium bromide may be performed to evaluate the quality of the nucleic acid extracted.

Analysis of Recovered Nucleic Acid

The genomic nucleic acid content of an individual animal or human represents a highly individualized biological substance that is unique to that individual. Indeed, the genes encoded by the genomic DNA, their patterns of expression, and unique rearrangements that occur during meiosis influence to a large extent the very traits that make each individual unique, and may be employed as a genetic identification method. Storage of genomic DNA in largely intact form would thus represent storage of the very substance that makes each individual unique, and may be employed as a means of genetic identification (Begovich et al., supra; Erlich et al., supra; Kawasaki et al., *Methods in Enzymology*, 218, 369 (1993)). With the rising popularity of cremation as a means of disposing of the human or animal corpse, all traces of the genetic content are destroyed by oxidation. Accordingly, a method of preserving genomic nucleic acid in intact form could become desirable for identification or maintaining a verifiably unique heirloom.

Thus, nucleic acid recovered from a device or receptacle of the invention, present in largely intact form, may be used for retrospective genetic analysis. This analysis may be useful for genetic testing for disease susceptibility, parentage testing, or for testing of familial lineages for continuity. The latter two categories of testing can be important in estate, probate, and child support matters to identify proper blood relatives accurately. The former category of testing may also become important as science and medicine acquire knowledge regarding the genetic basis for inherited diseases and genetic predispositions to disease susceptibility, (Begovich et al., supra; Marian, *Chest*, 108, 255 (1995); Markham, *BMT*, 3, 441 (1993)) or to confirm the presence of a particular infectious disease that had not yet been identified or characterized at the time the nucleic acid sample was obtained. The ability to test intact genomic DNA from family members of an affected individual can provide valuable insights into mechanisms of inheritance and may become useful in the management of the disease, particularly as science and medicine begin to understand the interaction of various genes on disease pathogenesis.

Recovered nucleic acid may be analyzed by Southern blot, RFLP or PCR analysis (for recovered genomic or cDNA) or Northern blot or RT-PCR analysis (for recovered RNA), by methods well known to the art. See, for example, Sambrook et al., supra (1989), Marian, supra, and Markham, supra. The methodology employed is dependent on the genetic information sought, e.g., the presence of a translocation, insertion or deletion, and the amount of nucleic acid recovered. Thus, to identify a point mutation in a gene, the recovered genomic DNA or cDNA may be amplified in a PCR with primers specific for the gene and the PCR product sequenced, or the recovered genomic DNA mixed with a restriction endonuclease which detects the base mutation and then subjected to electrophoretic analysis, optionally employing Southern blot, to detect the presence of the mutated gene.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method for long-term maintenance of intact nucleic acid comprising:

(a) introducing an amount of isolated mammalian nucleic acid and an inert gas into a cavity of a receptacle;

(b) introducing a fastener into the aperture of the cavity to form a nucleic acid containing receptacle, wherein the fastener retains the nucleic acid in the cavity;

(c) introducing the nucleic acid containing receptacle into a cavity of a storage device, and wherein either the receptacle or storage device is formed of a natural material; and (d) introducing a sealant into the aperture of the cavity of the device to form a nucleic acid storage device, wherein the sealant retains the nucleic acid containing receptacle in the cavity of the device.

2. A method for long-term maintenance of intact nucleic acid, comprising:

(a) introducing a nucleic acid containing receptacle into a cavity of a storage device, wherein the nucleic acid containing receptacle comprises an amount of isolated mammalian nucleic acid in a cavity of the receptacle which contains an inert gas, wherein either the receptacle or storage device is formed of a natural material, and wherein the nucleic acid is retained in the cavity by a fastener; and (b) introducing a sealant into the aperture of the cavity of the device to form a nucleic acid storage device, wherein the sealant retains the nucleic acid containing receptacle in the cavity of the device.

3. The method of claim 1 or 2 wherein the isolated nucleic acid is genomic DNA, RNA or cDNA obtained from RNA.

4. The method of claim 1 or 2 wherein the receptacle is formed from a synthetic polymer.

5. The method of claim 1 or 2 wherein the receptacle is formed from a natural material.

6. The method of claim 5 wherein the material is amber, copal, natural pearl or cultured pearl.

7. The method of claim 1 or 2 wherein the device is formed from a material that inhibits oxidation or depurination of nucleic acid.

8. The method of claim 7 wherein the material is amber or copal.

9. The method of claim 1 or 2 wherein the sealant is a resin.

10. The method of claim 9 wherein the resin is epoxy or molten copal.

11. The method of claim 1 or 2 wherein more than one nucleic acid receptacle is introduced to the device.

12. The method of claim 1 wherein the nucleic acid is human nucleic acid.

13. A nucleic acid storage device prepared by the method of claim 1 or 2.

14. A method to prepare a receptacle for long-term storage of nucleic acid, comprising:

(a) introducing an amount of isolated mammalian nucleic acid and an inert gas into a cavity of the receptacle, wherein the receptacle is formed from amber, copal, natural pearl or cultured pearl; and (b) introducing a sealant into the aperture of the cavity to form a nucleic acid containing receptacle, wherein the sealant retains the nucleic acid in the cavity.

15. A nucleic acid containing receptacle prepared by the method of claim 14.

* * * * *

UNITED STATES PATENT AND TRADEMARK OFFICE
CERTIFICATE OF CORRECTION

PATENT NO. : 6,258,320 B1
DATED : July 10, 2001
INVENTOR(S) : David H. Persing and Susan H. Persing It is certified that error appears in the above-identified patent and that said Letters Patent is hereby corrected as shown below:

Column 1,
Line 28, delete "Endeayor" and insert -- Endeavor --, therefor.
Line 30, delete "Experieltia" and insert -- Experientia --, therefor.

Column 6,
Line 17, insert -- ¶ As used herein, a "fastening means" includes a jewelry screw, stop or other machined capping device -- after "plastic".
Line 21, delete extra spacing after "90%".

Signed and Sealed this

Twenty-third Day of April, 2002

*Attest:*

*Attesting Officer*

JAMES E. ROGAN
*Director of the United States Patent and Trademark Office*